US011227682B2

(12) United States Patent
Huang

(10) Patent No.: US 11,227,682 B2
(45) Date of Patent: Jan. 18, 2022

(54) ATOMIZATION SYSTEM AND METHOD HAVING AUTHENTICATION MECHANISM

(71) Applicant: HCMed Innovations Co., LTD., Taipei (TW)

(72) Inventor: Chih-Ping Huang, New Taipei (TW)

(73) Assignee: HCMed Innovations Co., LTD., Taipei (TW)

(*) Notice: Subject to any disclaimer, the term of this patent is extended or adjusted under 35 U.S.C. 154(b) by 314 days.

(21) Appl. No.: 16/367,199

(22) Filed: Mar. 27, 2019

(65) Prior Publication Data

US 2020/0185077 A1 Jun. 11, 2020

(30) Foreign Application Priority Data

Dec. 5, 2018 (TW) ................................ 107143638

(51) Int. Cl.
*G16H 20/13* (2018.01)
*G06K 7/14* (2006.01)
(Continued)

(52) U.S. Cl.
CPC ........... *G16H 20/13* (2018.01); *A61B 5/1172* (2013.01); *A61B 5/1176* (2013.01); *A61M 11/00* (2013.01); *G06K 7/1417* (2013.01); *G06Q 30/0185* (2013.01); *A61M 2205/3553* (2013.01); *A61M 2205/3569* (2013.01);
(Continued)

(58) Field of Classification Search
CPC ........ G16H 20/13; G16H 40/63; G16H 40/67; G06K 7/1417; G06K 19/0728; G06Q 30/0185; A61B 5/1172; A61B 5/1176; A61M 11/00; A61M 2205/3569; A61M 2205/3553; A61M 2205/6063; A61M 2205/6072; A61M 2205/609; A61M 2205/3375; A61M 2205/505; A61M 15/00; A61M 2205/276; A61M 2205/43
See application file for complete search history.

(56) References Cited

U.S. PATENT DOCUMENTS

| | | | | |
|---|---|---|---|---|
| 2005/0172954 A1* | 8/2005 | Smith | ............... | A61M 15/0028 128/200.14 |
| 2010/0326436 A1* | 12/2010 | Kaneko | ............... | A61M 15/009 128/203.12 |
| 2018/0077546 A1* | 3/2018 | Arunachalam | ........ | B60Q 9/008 |

FOREIGN PATENT DOCUMENTS

| | | |
|---|---|---|
| CN | 108172227 A | 6/2018 |
| CN | 208110302 U | 11/2018 |

(Continued)

*Primary Examiner* — Matthew Mikels
(74) *Attorney, Agent, or Firm* — Li & Cai Intellectual Property Office

(57) ABSTRACT

An atomization system and an atomization method are provided. The atomization system having an authentication mechanism includes an atomized drug container, a user device, and an atomizing device. The user device includes a communication module, an optical authentication module and a first acoustic wave communication module. The optical authentication module is configured to perform a first optical authentication operation associated with an authentication code carrier to obtain first optical authentication information, and the communication module is configured to request a cloud server to perform an authentication operation for the first optical authentication information to determine the authenticity of the atomized drug container.

18 Claims, 8 Drawing Sheets

(51) Int. Cl.
*G06Q 30/00* (2012.01)
*A61B 5/1172* (2016.01)
*A61B 5/1171* (2016.01)
*A61M 11/00* (2006.01)

(52) U.S. Cl.
CPC ............... *A61M 2205/3584* (2013.01); *A61M 2205/609* (2013.01); *A61M 2205/6063* (2013.01); *A61M 2205/6072* (2013.01)

(56) References Cited

FOREIGN PATENT DOCUMENTS

| | | |
|---|---|---|
| TW | M564292 U | 7/2018 |
| TW | M564293 U | 7/2018 |

* cited by examiner

ATOMIZATION SYSTEM AND METHOD HAVING AUTHENTICATION MECHANISM

CROSS-REFERENCE TO RELATED PATENT APPLICATION

This application claims the benefit of priority to Taiwan Patent Application No. 107143638, filed on Dec. 5, 2018. The entire content of the above identified application is incorporated herein by reference.

Some references, which may include patents, patent applications and various publications, may be cited and discussed in the description of this disclosure. The citation and/or discussion of such references is provided merely to clarify the description of the present disclosure and is not an admission that any such reference is "prior art" to the disclosure described herein. All references cited and discussed in this specification are incorporated herein by reference in their entireties and to the same extent as if each reference was individually incorporated by reference.

FIELD OF THE DISCLOSURE

The present application relates to an atomization system and a method, in particular to an atomization system and a method having an authentication mechanism.

BACKGROUND OF THE DISCLOSURE

Medical nebulizers are mainly used for administration via the respiratory system. The nebulizer atomizes a liquid into fine particles with a certain particle size, and a medicament can be delivered from a patient's mouth and nose to enter the respiratory system of the patient through breathing, so that the therapeutic purpose can be achieved through the circulatory system.

However, due to high prices of commercially available medicines, some unscrupulous businessmen are attracted to counterfeit medicines. Since product fraud is easy and the illegal income is high, the forgery of medicines has never stopped in both domestic and overseas markets.

For example, anti-counterfeiting techniques mainly used by domestic and overseas pharmaceutical companies include using one-dimensional/two-dimensional barcode labels, laser tags, anti-counterfeit bottle caps, and anti-counterfeit ink printings on labels on the outside of pharmaceutical packaging or pharmaceuticals, in order to increase the difficulty of counterfeiting, and to prevent counterfeit medicine by increasing counterfeit costs. Still, since these anti-counterfeiting techniques can easily be achieved by counterfeiters, the forgery of such medicines cannot be completely eradicated.

Moreover, counterfeit medicines may also cause physical harm to consumers, even resulting in loss of lives and properties. Therefore, there is a need for an atomization system and devices that can improve the existing anti-counterfeiting mechanisms and ensure that consumers do not use counterfeit medicines.

SUMMARY OF THE DISCLOSURE

In response to the above-referenced technical inadequacies, the present disclosure provides an atomization system and device having an authentication mechanism.

In one aspect, the present disclosure provides an atomization system having an authentication mechanism, which includes at least one atomized medicine container, a user device and an atomization device. The at least one atomized medicine container has an authentication code carrier associated with the at least one atomized medicine container, and the at least one atomized medicine container contains an atomized medicine. The user device includes a communication module, an optical authentication module and a first acoustic wave communication module. The communication module is configured to connect with a cloud server through a network. The optical authentication module is configured to perform a first optical authentication operation related to the authentication code carrier to obtain first optical authentication information. The communication module is configured to request the cloud server to perform an authentication operation for the first optical authentication information for determining an authenticity of the at least one atomized medicine container. After the authentication operation is completed, the cloud server returns an authentication success signal. The first acoustic wave communication module is configured to encode an atomizing device activation signal into a first acoustic wave signal to be transmitted when the communication module receives the authentication success signal. The atomization device includes an atomization module, a second acoustic communication module and a control module. The atomization module has an accommodating portion for accommodating the atomized medicine and an atomization element for atomizing the atomized medicine placed in the accommodating portion. The second acoustic communication module is configured to receive the first acoustic signal, and decode the first acoustic signal to produce a starting signal for the atomization device. The control module is configured to control the atomization module to atomize the atomized medicine according to the starting signal for the atomization device.

In another aspect, an atomization method having an authentication mechanism includes: placing an atomized medicine contained in at least one atomized medicine container into a containing portion of an atomizing device; configuring a communication module of a user device to connect with a cloud server through a network; configuring an optical authentication module of the user device to perform an optical authentication operation related to the authentication code carrier to obtain first optical authentication information; configuring the communication module to request the cloud server to perform the authentication operation for the first optical authentication information to determine an authenticity of the atomized medicine container, and after the authentication operation is completed, configuring the cloud server to return the authentication success signal; configuring a first acoustic wave communication module to encode an atomizing device activation signal into a first acoustic wave signal to be transmitted when the communication module receives the authentication success signal; configuring a second acoustic communication module of the atomization device to receive the first acoustic signal, and decode the first acoustic signal to produce a starting signal for the atomization device; and configuring a control module of the atomization device to control the atomization module to atomize the atomized medicine according to the starting signal for the atomization device.

One of the advantages of the present disclosure is that the atomization system and method having the authentication mechanism provided by the present disclosure may improve the anti-fake effects for the anti-counterfeit identification code and product history data through a combination of the optical authentication module and the identification code carrier having the optical authentication information.

In addition, the technology of the present disclosure can utilize the common audio system to implement an information authentication and acoustic wave communication functions between the user device and the atomization device. By utilizing a device having an audio-related circuit built therein, the present disclosure can utilize the existing audio-related circuit to further communicate with the atomization device, thereby improving the security of the authentication mechanism and making it easier for users to use.

Furthermore, in the atomization system and method having the authentication mechanism of the present disclosure, the camera, the video camera or the fingerprint recognition module of the existing smart phone can be used to capture the gesture or biometric feature of the user as the second optical authentication information, and the authentication operation can be performed to ensure security before the first authentication operation is performed.

In addition, an authentication information input interface is additionally provided for the user to input the authentication information on the authentication code carrier, which further increases the flexibility of the authentication method.

For a better understanding of the features and technical content of the present application, reference should be made to the following detailed description and drawings of the present application. However, the drawings are provided for the purpose of providing references and illustrations only, and are not intended to limit the present application.

These and other aspects of the present disclosure will become apparent from the following description of the embodiment taken in conjunction with the following drawings and their captions, although variations and modifications therein may be affected without departing from the spirit and scope of the novel concepts of the disclosure.

BRIEF DESCRIPTION OF THE DRAWINGS

The present disclosure will become more fully understood from the following detailed description and accompanying drawings.

DETAILED DESCRIPTION OF THE EXEMPLARY EMBODIMENTS

Figure 1:
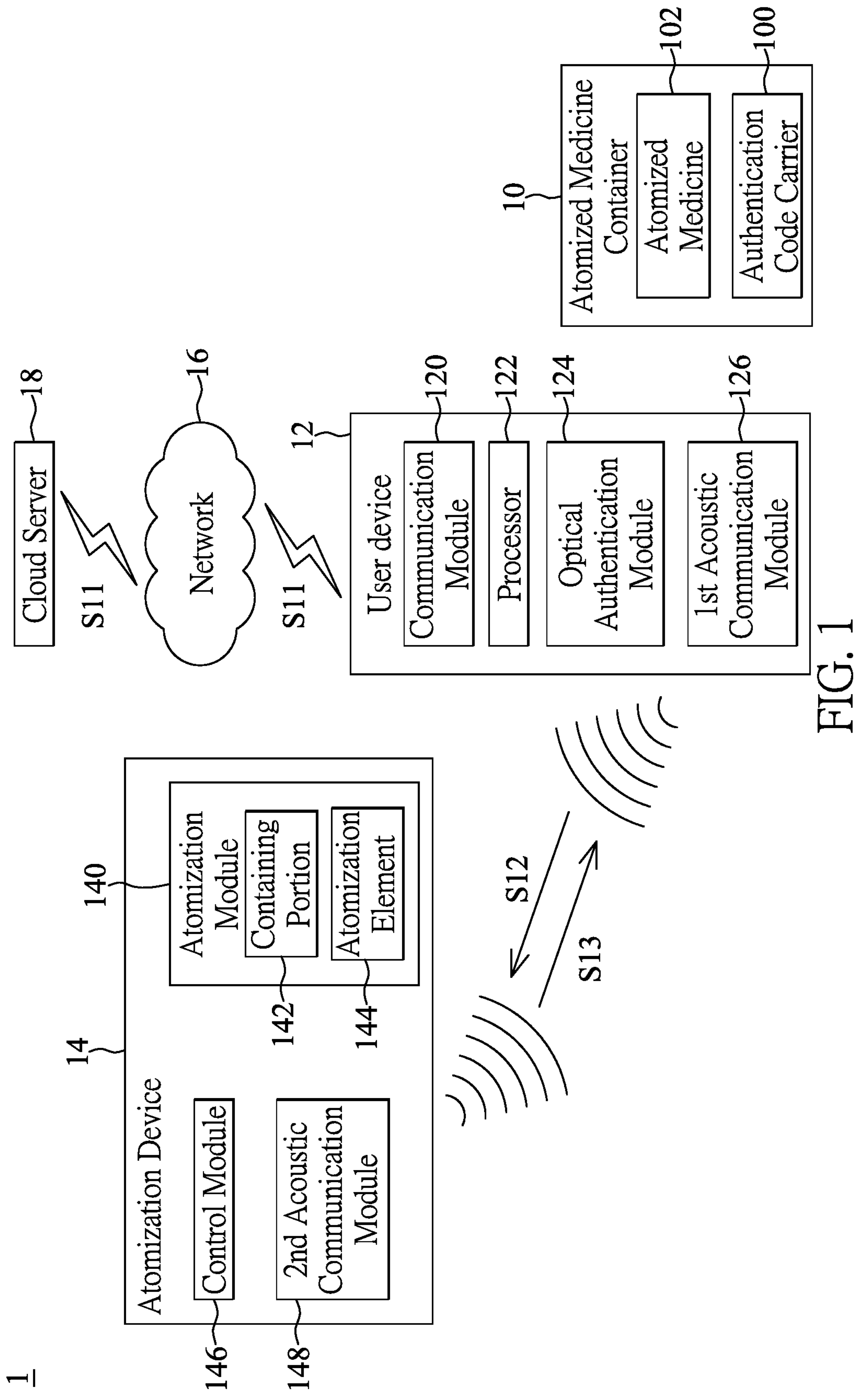
FIG. 1 is a block diagram of an atomization system having an authentication mechanism according to a first embodiment of the present disclosure.

The present disclosure is more particularly described in the following examples that are intended as illustrative only since numerous modifications and variations therein will be apparent to those skilled in the art. Like numbers in the drawings indicate like components throughout the views. As used in the description herein and throughout the claims that follow, unless the context clearly dictates otherwise, the meaning of "a", "an", and "the" includes plural reference, and the meaning of "in" includes "in" and "on". Titles or subtitles can be used herein for the convenience of a reader, which shall have no influence on the scope of the present disclosure.

The terms used herein generally have their ordinary meanings in the art. In the case of conflict, the present document, including any definitions given herein, will prevail. The same thing can be expressed in more than one way. Alternative language and synonyms can be used for any term(s) discussed herein, and no special significance is to be placed upon whether a term is elaborated or discussed herein. A recital of one or more synonyms does not exclude the use of other synonyms. The use of examples anywhere in this specification including examples of any terms is illustrative only, and in no way limits the scope and meaning of the present disclosure or of any exemplified term. Likewise, the present disclosure is not limited to various embodiments given herein. Numbering terms such as "first", "second" or "third" can be used to describe various components, signals or the like, which are for distinguishing one component/signal from another one only, and are not intended to, nor should be construed to impose any substantive limitations on the components, signals or the like.

The following is embodiments of the present application disclosed in relation to the "atomization system and method having an authentication mechanism" through specific embodiments. Those skilled in the art can understand the advantages and effects of the present application according to the contents disclosed in the present specification. The present application may be implemented or applied through other different specific embodiments. The details in this specification may also be based on different viewpoints and applications, and various modifications and changes may be made without departing from the concept of the present application. In addition, the drawings of the present application are merely schematic illustrations and are not depicted by actual dimensions. The following embodiments will further describe related technical contents of the present application in detail, but the disclosed contents are not intended to limit the scope of the present application.

It will be understood that although the terms first, second, third, etc. may be used herein to describe various elements or signals, however, these elements or signals should not be limited by these terms. These terms are mainly used to distinguish one element from another element, or one signal from another signal. In addition, the term "or" as used herein, as appropriate, may include combinations of any one or more of the associated listed items.

To clarify, in some cases, the techniques of the present application may be presented as including separate functional blocks that include functional blocks, including devices, device elements, steps or routes in a method implemented in software, or a combination of hardware and software.

In some embodiments, computer-readable storage devices, media, and memory may include cables or wireless signals containing bit streams and so on. However, when mentioned, non-transitory computer-readable storage media explicitly excludes media such as energy, carrier signals, electromagnetic waves, and signals themselves.

The method according to the above-described embodiments may be implemented by using computer-executed instructions stored or otherwise accessible from a computer-readable medium. Such instructions may include, for example, instructions and data that cause or otherwise configure a general purpose computer, a special purpose computer, or a special purpose processing device to perform a certain function or set of functions. Parts of the computer resources used can be accessed via the Internet. The computer executable instructions may be, for example, binary, intermediate format instructions such as assembly language, firmware, or source code. Examples of computer-readable media that may be used to store instructions, information used, and/or information created during a method in accordance with the described embodiments include a magnetic or optical disk, flash memory, non-volatile memory USB memory devices, networked storage devices, and more.

Devices for implementing these disclosed methods may include hardware, firmware, and/or software, and may take any of a variety of configurations. Typical examples of such configurations include laptops, smart phones, small personal computers, personal digital assistants, and the like. The functions described herein may also be implemented in peripheral devices or built-in cards. By way of further example, such functions may also be implemented on circuit boards executing different processes on different chips or on a single device.

The instructions, media for communicating such instructions, computing resources for performing the same or other structures for supporting such computing resources are used for providing means of the functionality described in these publications.

First Embodiment

FIG. 1 is a block diagram of an atomization system having an authentication mechanism according to a first embodiment of the present disclosure. Reference is now made to FIG. 1. The first embodiment of the present application provides an atomization system 1 having an authentication mechanism, which includes an atomized medicine container 10, a user device 12, and an atomization device 14.

The atomized medicine container 10 has an authentication code carrier 100 associated with the atomized medicine container 10 and contains the atomized medicine 102. In general, the atomized medicine container 10 can be a bottle container with a bottle rim, and the authentication code carrier 100 can be an authentication tag provided on the bottle cap to be used separately from the bottle container, but the present disclosure is not limited thereto. The authentication code carrier 100 can also be an authentication tag detachably disposed outside the bottle container.

Referring to FIG. 1, the user device 12 includes a communication module 120, a processor 122, an optical authentication module 124, and a first acoustic wave communication module 126. In the present application, examples are not limited by the prerequisite of an embodiment, further examples of various embodiments in a wide variety of operating environments, which can include any number of applications that can be used to operate one or more server computers, user computers or computing devices. The user device 12 can include any number of general-purpose personal computers running standard operating systems, such as laptops or notebooks, and mobile phones, wireless phones and hand-held devices that execute mobile software and capable of supporting a large number of Internet and messaging communication protocols. Such system may also include a number of workstations, running any of a variety of commercially available operating systems for development and database management purposes, and other known applications. These devices may also include other electronic devices capable of communicating through the network, such as virtual terminals, host-clients, gaming systems, and other devices.

Functions of the processor 122 included in the user device 12 may be implemented by using one or more processors. The processor 122 can be a programmable unit such as a microprocessor, a microcontroller, a digital signal processor (DSP) chip, a field-programmable gate array (FPGA), or the like. Functions of the processor may also be implemented by one or several electronic devices or ICs. In other words, the functions performed by the processor 122 may be implemented in a hardware domain or a software domain or a combination of the hardware domain and the software domain.

The communication module 120 is connected to the cloud server 18 through the network 16. Here, the communication module 120 can be connected to the network 16 through a near-end network transmission, such as WIFI, Bluetooth, etc., and communicate with the cloud server 18. In addition, in the example using the cloud server 18, the cloud server 18 can operate any of various server or mid-tier applications including HTTP servers, FTP servers, CGI servers, data servers, Java servers and business application servers. The cloud server 18 may also execute programs or scripts to respond to requests from the user devices. For example, by executing one or more web applications, it can be implemented as one or more scripts written in any programming language, such as Java, C, C #, or C++ or any scripting language such as Perl, Python, or Tcl and combinations thereof. In addition, the cloud server 18 can also include a database server.

The optical authentication module 124 is configured to perform an optical authentication operation related to the authentication code carrier 100 to obtain first optical authentication information. For example, the first optical authentication operation includes identifying, by the optical authentication module 124, an authentication code of the authentication code carrier 100 to obtain the first optical authentication information. The authentication code includes at least one of a barcode, a QR code, and a dot matrix pattern.

After the first optical authentication information is obtained, the communication module 120 can request the cloud server 18 to perform an authentication operation for the first optical authentication information to determine the authenticity of the atomized medicine container 10. After the authentication operation is completed, the cloud server 18 returns an authentication success signal S11 to notify the user device 12 that the atomized medicine container 10 is authentic.

In addition, the user device 12 further includes a first acoustic wave communication module 126 for encoding a starting signal for the atomization device into the first acoustic wave signal S12 to be transmitted when the communication module 120 receives the authentication success signal S11.

The atomization device 14 includes an atomization module 140, a second acoustic communication module 148 and a control module 146. The atomization module has an accommodating portion 142 and an atomization element 144, the accommodating portion 142 is utilized for accommodating the atomized medicine, and the atomization element 144 is utilized for atomizing the atomized medicine 102 placed in the accommodating portion 142.

The second acoustic communication module 148 is configured to receive the first acoustic signal S12, and decode the first acoustic signal S12 to produce a starting signal for the atomization device 14. The control module 146 is configured to control the atomization module 140 to atomize the atomized medicine 102 according to the starting signal for the atomization device 14. Similarly, the functionality of the control module 146 included in the atomization device 14 can be implemented using one or more processing units. The processor 122 can be a programmable unit such as a microprocessor, a microcontroller, a digital signal processor (DSP) chip, a field-programmable gate array (FPGA), or the like. Functions of the processor may also be implemented by one or several electronic devices or ICs. In other words, the functions performed by the control module 146 may be implemented in a hardware domain or a software domain or a combination of the hardware domain and the software domain.

Furthermore, after the control module 146 controls the atomization module 140 to atomize the atomized medicine 102, the control module 146 further generates a starting state signal, the second acoustic communication module 148 encodes the starting state signal into a second acoustic signal S13 to be transmitted, the first acoustic communication module 126 receives and decodes the second acoustic signal S13 to display a starting state of the atomization device 14 on the user device 12.

Figure 2:
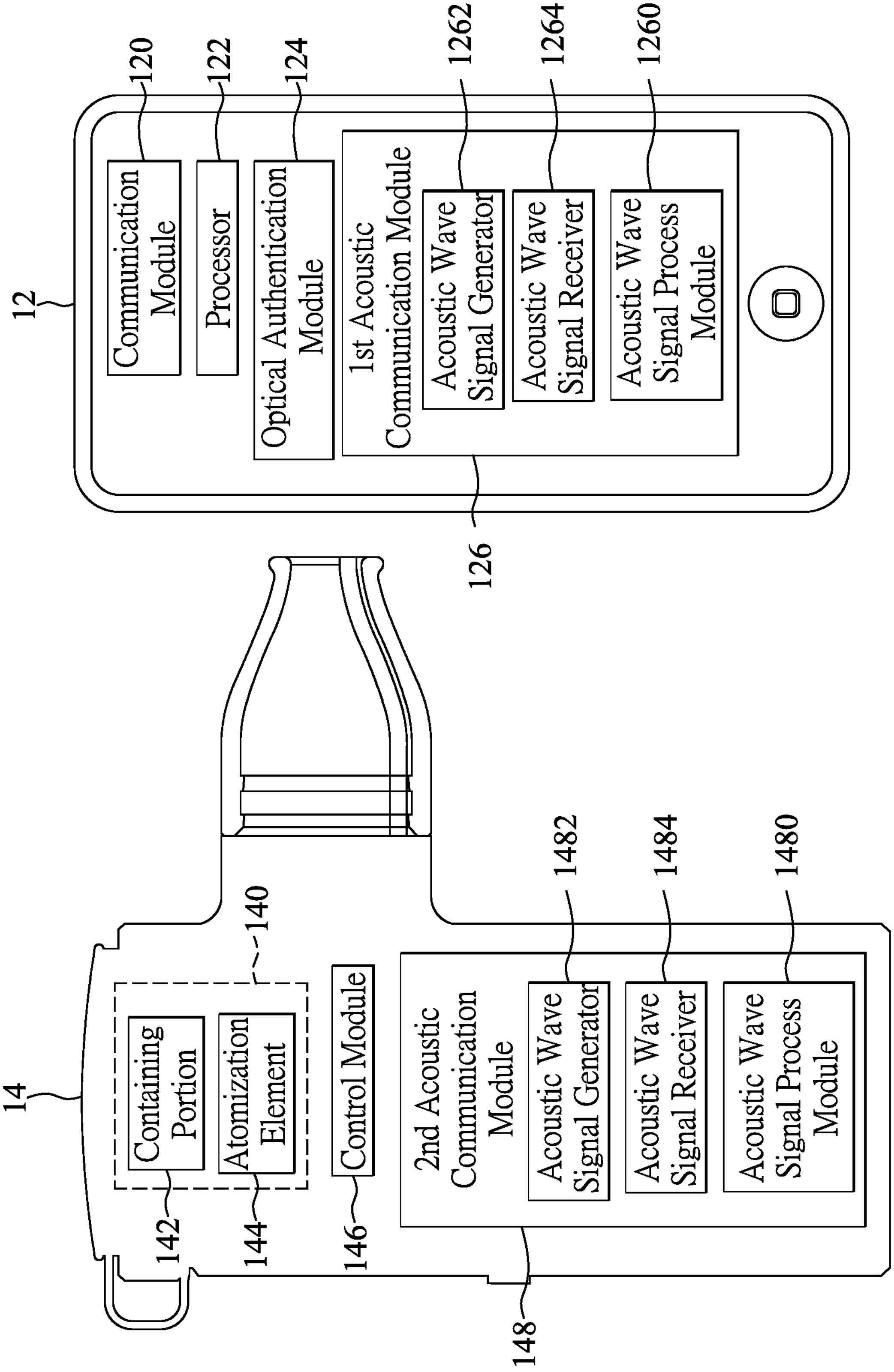
FIG. 2 is a functional diagram of the atomization system having the authentication mechanism according to the first embodiment of the present disclosure.

FIG. 2 is a functional diagram of the atomization system having the authentication mechanism according to the first embodiment of the present disclosure. As shown in FIG. 2, in the atomization system 1 having an authentication mechanism, the first acoustic wave communication module 126 includes an acoustic wave signal generator 1262, an acoustic wave signal receiver 1264, and an acoustic wave signal process module 1260. The acoustic wave signal processing module 1262 is configured to decode the received acoustic wave signals to generate a signal, and encode the signal to generate an acoustic wave signal.

For example, the acoustic signal processing module 1260 in the first acoustic wave communication module 126 of the present disclosure can modulate the communication signal into a high frequency acoustic wave, for example, the ultrasonic/ultrasonic wave frequency range, which is higher than the audio sound wave frequency range. The acoustic wave is then transmitted by the acoustic wave signal generator 1262. On the other hand, the first acoustic wave communication module 126 can also receive the high frequency sound wave by using the acoustic wave signal receiver 1264, and the high frequency acoustic wave is then demodulated by the acoustic wave signal process module 1260 to retrieve the communication signal therein, and the user device 12 can operate and interact according to the communication signal, and the communication function between the atomization device 14 and the user device 12 can be achieved.

Therefore, the second acoustic communication module 148 of the atomization device 14 also includes an acoustic wave signal generator 1482, an acoustic wave signal receiver 1484, and an acoustic wave signal process module 1480, and thus the repeated descriptions are omitted hereinafter. Specifically, the acoustic wave signals include at least one of an audible sound wave, an inaudible sound wave, a dual tone multi-frequency sound wave, and an ultrasonic wave. Corresponding to the case of using dual-tone multi-frequency acoustic waves, the first acoustic wave communication module 126 and the second acoustic wave communication module 148 may respectively be dual-tone multi-frequency sound wave transceivers, but the present disclosure is not limited thereto.

Figure 3A:
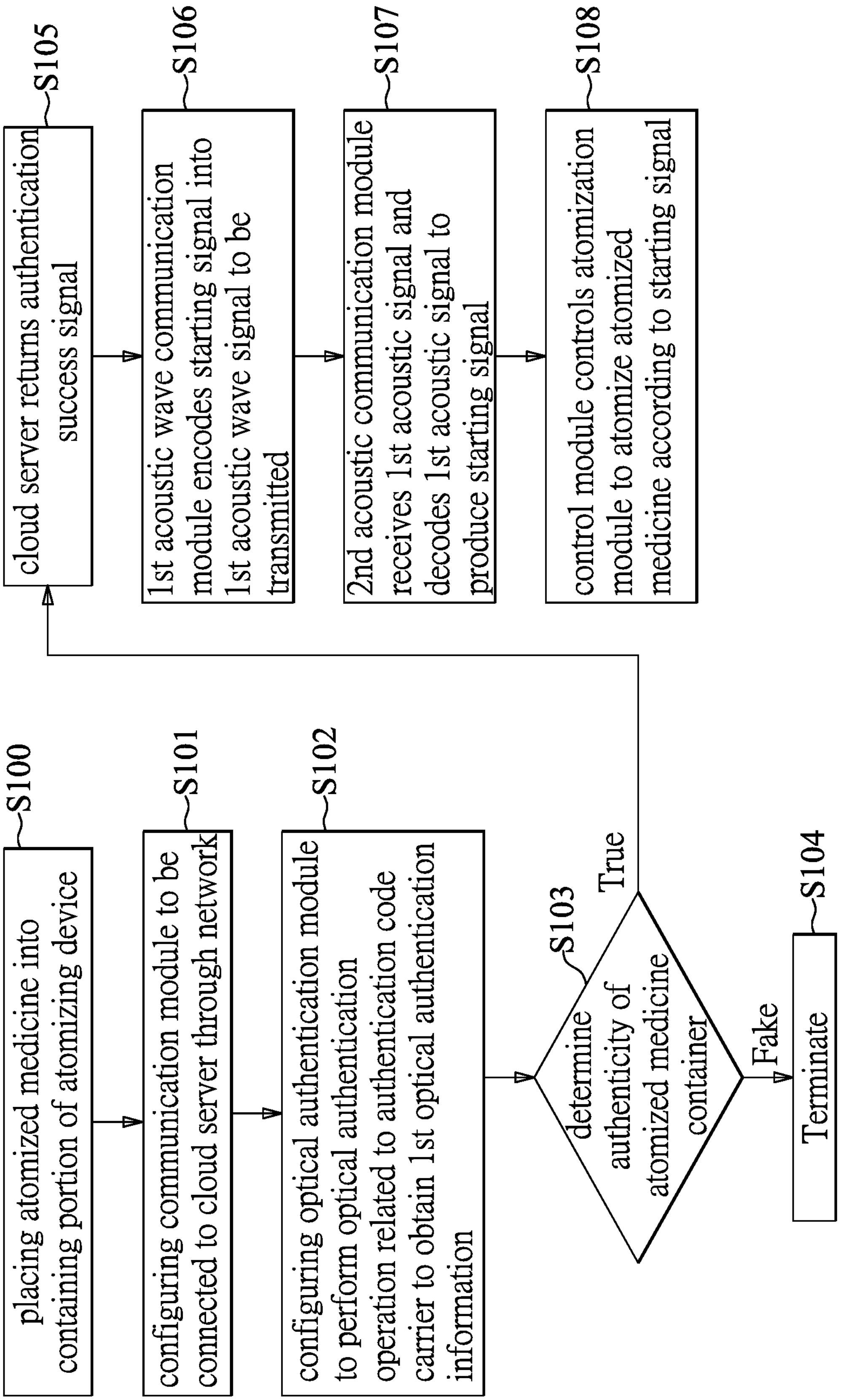
FIG. 3A is a flowchart of an atomization method having an authentication mechanism according to the first embodiment of the present disclosure.
Figure 3B:
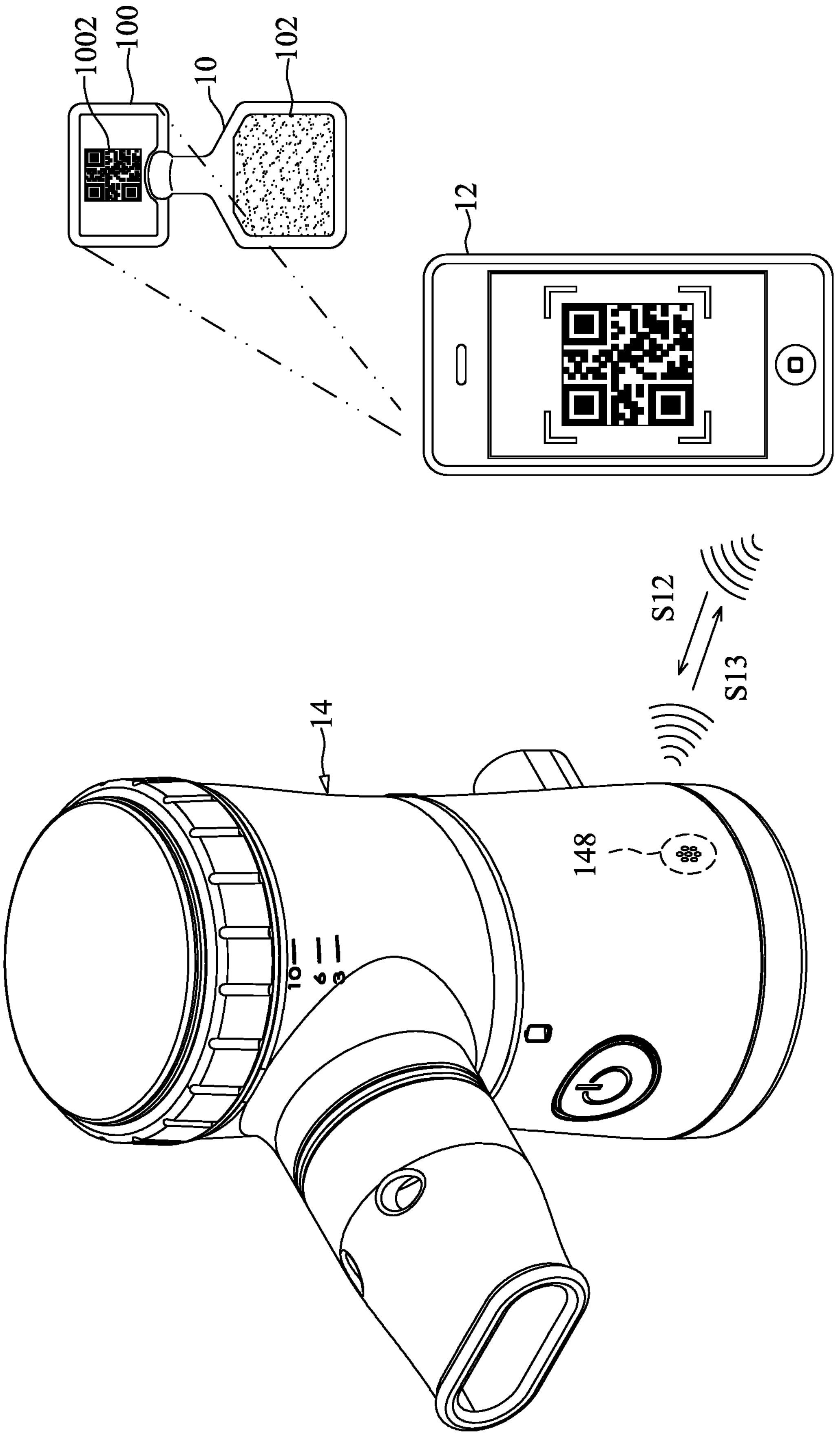
FIG. 3B is a schematic diagram showing an authentication operation of the atomization method having the authentication mechanism according to the first embodiment of the present disclosure.

FIG. 3A is a flowchart of an atomization method having an authentication mechanism according to the first embodiment of the present disclosure, and FIG. 3B is a schematic diagram showing an authentication operation of the atomization method having the authentication mechanism according to the first embodiment of the present disclosure. Reference is now made to FIGS. 3A and 3B, the first embodiment of the present disclosure further provides an atomization method having an authentication mechanism, which includes at least the following steps:

Step S100: placing an atomized medicine 102 into a containing portion 142 of an atomizing device 14.

Step S101: configuring the communication module 120 to be connected to the cloud server 18 through the network 16.

Step S102: configuring the optical authentication module 124 to perform an optical authentication operation related to the authentication code carrier 100 to obtain first optical authentication information. For example, the authentication tag 1002 on the authentication code carrier 100, such as at least one of a barcode, a QR code, and a dot matrix pattern, may be obtained, and the authentication tag 1002 may be identified or read by the optical authentication module 124 to obtain the first optical authentication information.

Step S103: configuring the cloud server 18 to determine authenticity of the atomized medicine container. More specifically, the communication module 120 can request the cloud server 18 to perform an authentication operation for the first optical authentication information to determine the authenticity of the atomized medicine container 10, and if the cloud server 18 determines that the atomized medicine container 10 is fake, the method proceeds to step S104 to terminate the authentication operation. If the cloud server 18 determines that the atomized medicine container 10 is authentic, the method proceeds to step S105.

Step S105: After the authentication operation is completed, the cloud server 18 returns an authentication success signal S11.

Step S106: Generating a starting signal for the atomization device 14 when the communication module 120 receives the authentication success signal S11, and configuring the first acoustic wave communication module S126 to encode the starting signal for the atomization device 14 into the first acoustic wave signal S12 to be transmitted.

Step S107: configuring the second acoustic communication module 148 of the atomization device 14 to receive the first acoustic signal S12, and decode the first acoustic signal S12 to produce a starting signal for the atomization device 14.

Step S108: configuring a control module 146 of the atomization device 14 to control the atomization module 140 to atomize the atomized medicine 102 according to the starting signal for the atomization device 14.

Figure 3C:
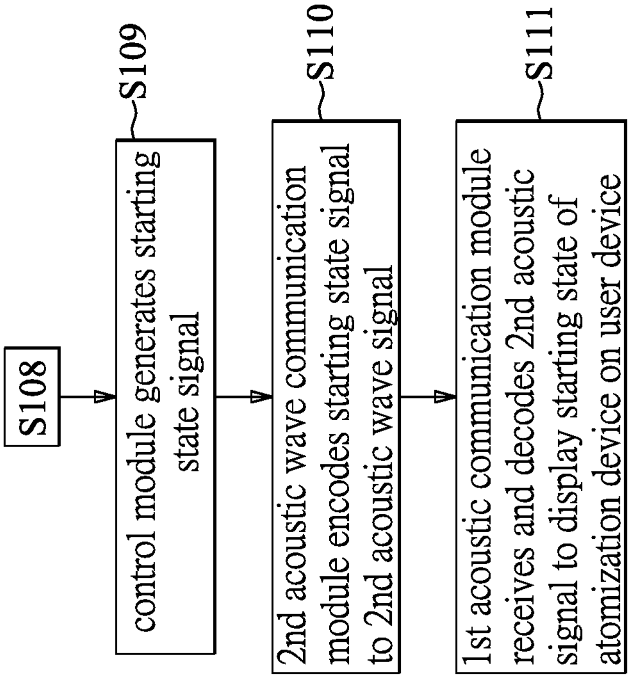
FIG. 3C is another flowchart of an atomization method having an authentication mechanism according to the first embodiment of the present disclosure.

Reference is now made to FIG. 3C, which is another flowchart of an atomization method having an authentication mechanism according to the first embodiment of the present disclosure. As shown in FIG. 3C, after step S108 is completed, the method can further include the following steps:

Step S109: configuring the control module 146 to generate a starting state signal. The starting state signal can carry information including a starting state of each component in the atomization device 14, or the remaining amount of the atomized medicine 102.

Step S110: configuring the second acoustic wave communication module to encode the starting state signal to a second acoustic wave signal S13 to be transmitted.

Step S111: configuring the first acoustic communication module 126 to receive and decode the second acoustic signal S13 to display a starting state of the atomization device 14 on the user device.

Therefore, in the atomization method having the authentication mechanism of the present disclosure, the improved anti-fake effects for the anti-counterfeit identification code and product history data can be achieved through a combination of the optical authentication module and the identification code carrier having the optical authentication information.

In addition, the technology of the present disclosure can utilize the common audio system to implement an information authentication and acoustic wave communication functions between the user device and the atomization device. By utilizing a device having an audio-related circuit built therein, the present disclosure can utilize the existing audio-related circuit to further communicate with the atomization device, thereby improving the security of the authentication mechanism and making it easier for users to use.

Second Embodiment

Figure 4:
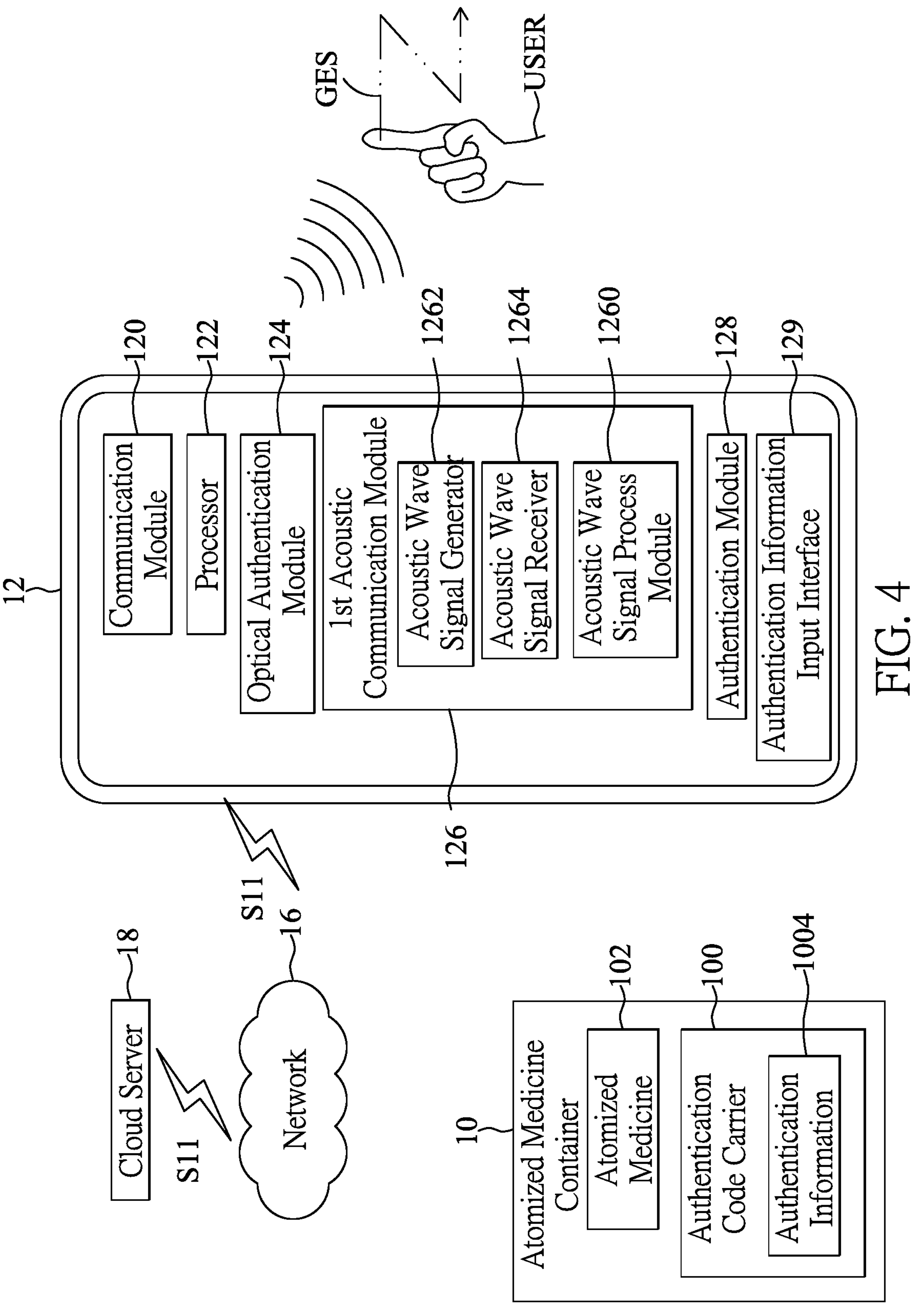
FIG. 4 is another functional diagram of the atomization system having the authentication mechanism according to the first embodiment of the present disclosure.

FIG. 4 is another functional diagram of the atomization system having the authentication mechanism according to the first embodiment of the present disclosure. As shown in FIG. 4, the user device 12 further includes an authentication module 128, and the optical authentication module 124 can perform a second optical authentication operation associated with the user USER to obtain second optical authentication information. More specifically, the authentication module 128 is configured to perform an authentication operation for the second optical authentication information. After the authentication operation is completed, the user device 12 can perform the first authentication operation mentioned above. The second optical authentication operation may include at least one of gesture authentication, facial recognition authentication, and fingerprint identification authentication. As shown in FIG. 4, the camera or the video camera of the existing smart phone can be used to capture the gesture GES of the user USER as the second optical authentication information, and the authentication operation is performed for the gesture GES. A database in the user device 12 can store a plurality of gestures defined by the owner of the atomizing device 14 to perform the authentication operation before the first authentication operation to ensure security.

On the other hand, the user device 12 further includes an authentication information input interface 129 for the user USER to input the authentication information 1004 on the authentication code carrier 100, and then the communication module 120 can request the cloud server 18 to perform an authentication operation for the authentication information 1004 to determine the authenticity of the atomized medicine 102 or the atomized medicine container 10. After the authentication operation is completed, the cloud server 18 returns the authentication success signal S11. In the case that the communication module 120 has no communication capability and is not connected to the cloud server 18, the authentication module 128 can be used to perform the authentication operation for the authentication information 1004. For example, the authentication information 1004 can be compared with information in the database built in the user device 12 to determine the authenticity of the corresponding atomized medicine 102 or atomized medicine container 10 by the authentication information 1004. Here, the information in the database used for comparison may be attached to the application for the authentication, or after the application for the authentication is installed, the information can be downloaded or updated when the communication module 120 with communication capability is connected to the cloud server 18.

Figure 5A:
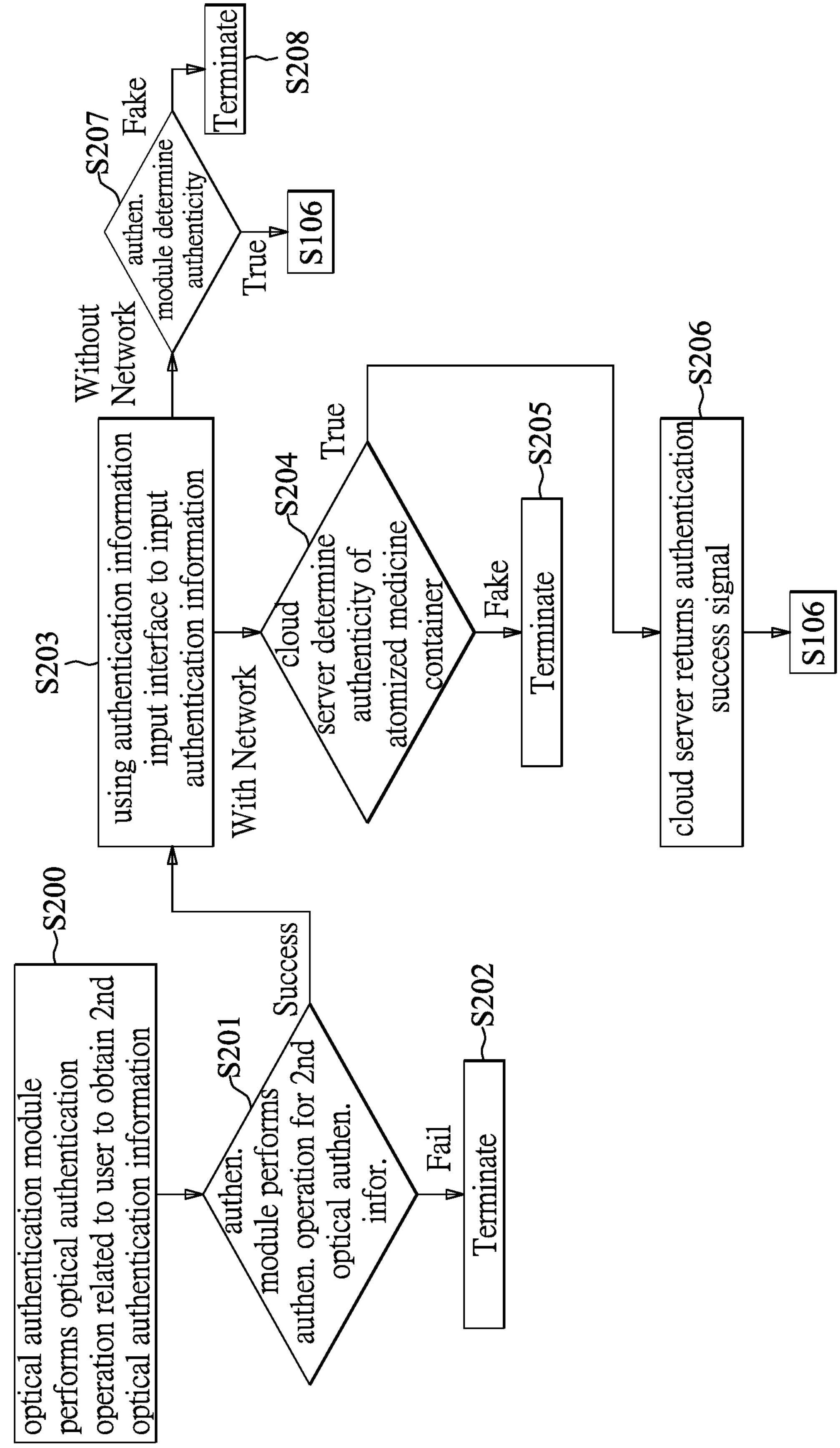
FIG. 5A is a flowchart of an atomization method having an authentication mechanism according to the second embodiment of the present disclosure.
Figure 5B:
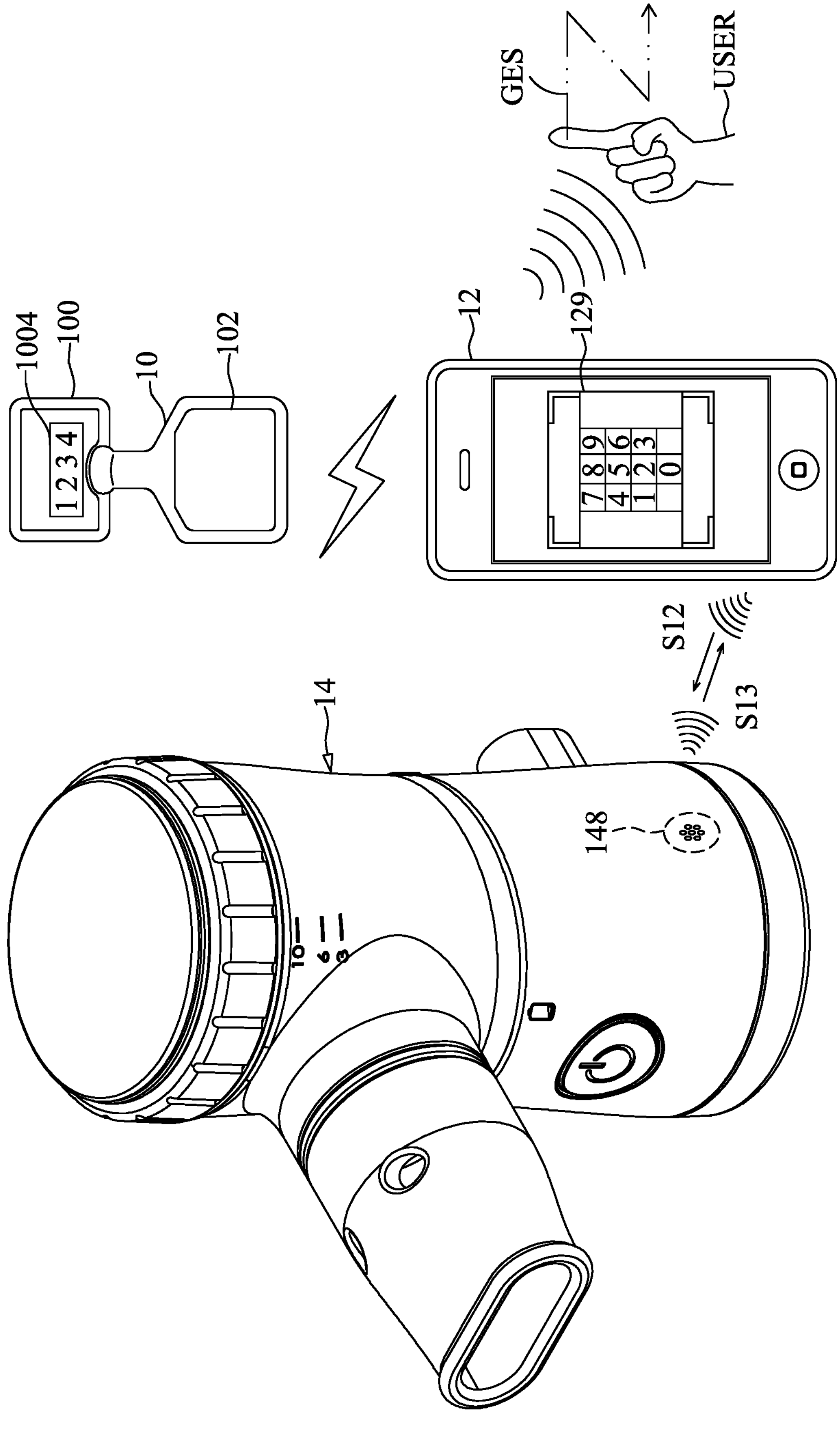
FIG. 5B is a schematic diagram showing an authentication operation of the atomization method having the authentication mechanism according to the second embodiment of the present disclosure.

FIG. 5A is a flowchart of an atomization method having an authentication mechanism according to the second embodiment of the present disclosure, and FIG. 5B is a schematic diagram showing an authentication operation of the atomization method having the authentication mechanism according to the second embodiment of the present disclosure. Reference is now made to FIGS. 5A and 5B, the second embodiment of the present disclosure further provides an atomization method having an authentication mechanism, which includes at least the following steps:

Step S200: configuring the optical authentication module 124 to perform an optical authentication operation related to the user USER to obtain a second optical authentication information.

Step S201: configuring the authentication module 128 to perform an authentication operation for the second optical authentication information. After the authentication operation is completed, the user device 12 can perform the first authentication operation. The second optical authentication operation can include at least one of gesture authentication, facial recognition authentication, and fingerprint identification authentication. If the authentication operation fails, the method proceeds to step S202, and the authentication operation is terminated. If the authentication is successful, the method proceeds to step S203.

Step S203: using the authentication information input interface 129 to input the authentication information 1004 on the authentication code carrier 100. The first acoustic wave communication module 126 of the user device 12 can also synchronously generate an acoustic wave signal corresponding to the authentication information 1004 to initiate the acoustic communication with the atomization device 14 while the user USER inputs the authentication information 1004. Here, when the communication module 120 has the communication capability and is connected to the cloud server 18, the method proceeds to step S204. If the communication module 120 has no communication capability and is not connected to the cloud server 18, the method proceeds to step S207.

Step S204: configuring the communication module 120 to request the cloud server 18 to perform the authentication operation for the authentication information 1004 to determine the authenticity of the atomized medicine container 10. If the cloud server 18 determines that the atomized medicine container 10 is fake, the method proceeds to step S205 to terminate the authentication operation. If the cloud server 18 determines that the atomized medicine container 10 is authentic, the method proceeds to step S206.

Step S206: After the authentication operation is completed, the cloud server 18 returns an authentication success signal S11, and the method proceeds to step S106 of FIG. 3A.

On the other hand, if the communication module 120 has no communication capability and is not connected to the cloud server 18, the method proceeds to step S207: configuring the authentication module 128 to perform the authentication operation for the authentication information 1004 to determine the authenticity of the atomized medicine container 10. As described above, the authentication information 1004 can be compared with the data in the database built in the user device 12 to determine the authenticity of the corresponding atomized medicine 102 or the atomized medicine container 10 according to the authentication information 1004. If the authentication module 128 determines that the atomized medicine container 10 is fake, the method proceeds to step S208 to terminate the authentication operation. If the authentication module 128 determines that the atomized medicine container 10 is authentic, the method proceeds to step S106 of FIG. 3A.

In some embodiments, steps S103 to S105 and steps S200 to S201 are not necessary, and step S203 may be directly performed to input to the authentication information 1004 on the identification code carrier 100 without performing the second optical authentication operation mentioned above.

Therefore, in the atomization system and method having the authentication mechanism of the present disclosure, the camera, the video camera or the fingerprint recognition module of the existing smart phone can be used to capture the gesture or biometric feature of the user as the second optical authentication information, and the authentication operation can be performed to ensure security before the first authentication operation is performed.

Furthermore, in addition to the authentication method provided in the first embodiment, the authentication information input interface is additionally provided for the user to input the authentication information on the authentication code carrier, which further increases the flexibility of the authentication method.

One of the advantages of the present disclosure is that the atomization system and method having the authentication mechanism provided by the present disclosure may improve the anti-fake effects for the anti-counterfeit identification code and product history data through a combination of the optical authentication module and the identification code carrier having the optical authentication information.

In addition, the technology of the present disclosure can utilize the common audio system to implement an information authentication and acoustic wave communication functions between the user device and the atomization device. By utilizing a device having an audio-related circuit built therein, the present disclosure can utilize the existing audio-related circuit to further communicate with the atomization device, thereby improving the security of the authentication mechanism and making it easier for users to use.

Furthermore, in the atomization system and method having the authentication mechanism of the present disclosure, the camera, the video camera or the fingerprint recognition module of the existing smart phone can be used to capture the gesture or biometric feature of the user as the second optical authentication information, and the authentication operation can be performed to ensure security before the first authentication operation is performed.

In addition, authentication information input interface is additionally provided for the user to input the authentication information on the authentication code carrier, which further increases the flexibility of the authentication method.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope.

What is claimed is:

1. An atomization system having an authentication mechanism, comprising:

at least one atomized medicine container having an authentication code carrier associated with the at least one atomized medicine container, the at least one atomized medicine container containing an atomized medicine;

a user device, including:

a communication module, configured to connect with a cloud server through a network;

an optical authentication module, configured to perform a first optical authentication operation related to the authentication code carrier to obtain first optical authentication information, wherein the communication module is configured to request the cloud server to perform an authentication operation for the first optical authentication information for determining authenticity of the at least one atomized medicine container, and after the authentication operation is completed, the cloud server returns an authentication success signal, wherein the cloud server is configured to execute programs or scripts to respond to a plurality of requests from the user device; and a first acoustic wave communication module, configured to encode an atomizing device activation signal into a first acoustic wave signal to be transmitted when the communication module receives the authentication success signal; and an atomization device, including:

an atomization module having an accommodating portion for accommodating the atomized medicine and an atomization element for atomizing the atomized medicine placed in the accommodating portion;

a second acoustic communication module connected to the control unit and configured to receive the first acoustic signal, and decode the first acoustic signal to produce a starting signal for the atomization device; and a control module, configured to control the atomization module to atomize the atomized medicine according to the starting signal for the atomization device;

wherein the optical authentication module is further configured to perform a second optical authentication operation associated with a user to obtain second optical authentication information;

wherein the second optical authentication operation includes at least one of gesture authentication, face recognition authentication, and fingerprint identification authentication.

2. The atomization system having the authentication mechanism according to claim 1, wherein the control module further generates a starting state signal after the control module controls the atomization module to atomize the atomized medicine, the second acoustic communication module encodes the starting state signal into a second acoustic signal to be transmitted, and the first acoustic communication module receives and decodes the second acoustic signal to display a starting state of the atomization device on the user device.

3. The atomization system having the authentication mechanism according to claim 1, wherein each of the first acoustic communication module and the second acoustic communication module includes:

an acoustic wave signal generator, configured to transmit acoustic wave signals;

an acoustic wave receiver, configured to receive acoustic wave signals; and an acoustic wave signal processing module, configured to decode the received acoustic wave signals to generate a signal, and encode the signal to generate an acoustic wave signal.

4. The atomization system having the authentication mechanism according to claim 3, wherein the acoustic wave signals include at least one of an audible sound wave, an inaudible sound wave, a dual tone multi-frequency sound wave, and an ultrasonic wave.

5. The atomization system having the authentication mechanism according to claim 1, wherein the first optical authentication operation includes: identifying, by the optical authentication module, an authentication code of the authentication code carrier to obtain the first optical authentication information.

6. The atomization system having the authentication mechanism according to claim 5, wherein the authentication code includes at least one of a barcode, a QR code, and a dot matrix pattern.

7. The atomization system having the authentication mechanism according to claim 1, wherein the user device further includes an authentication module, wherein the authentication module is configured to perform an authentication operation for the second optical authentication information, and the user device performs the first authentication operation after the authentication operation is completed.

8. The atomization system having the authentication mechanism according to claim 1, wherein the user device further includes an authentication information input interface for the user to input authentication information on the authentication code carrier, wherein the communication module is configured to request the cloud server to perform the authentication operation for the authentication information to determine the authenticity of the atomized medicine container, and after the authentication operation is completed, the cloud server returns the authentication success signal.

9. The atomization system having the authentication mechanism according to claim 1, wherein the user device further includes an authentication module and an authentication information input interface for the user to input an authentication information on the authentication code carrier, wherein the authentication module is configured to perform an authentication operation for the authentication information to determine the authenticity of the atomized medicine container, and after the authentication operation is completed, the first acoustic wave communication module is configured to directly encode the starting signal for the atomization device as the first acoustic signal to be transmitted.

10. An atomization method having an authentication mechanism, comprising:

placing an atomized medicine contained in at least one atomized medicine container into a containing portion of an atomizing device;

configuring a communication module of a user device to connect with a cloud server through a network;

configuring an optical authentication module of the user device to perform a first optical authentication operation related to an authentication code carrier to obtain first optical authentication information;

configuring the communication module to request the cloud server to perform the authentication operation for the first optical authentication information to determine authenticity of the atomized medicine container, and after the authentication operation is completed, configuring the cloud server to return the authentication success signal, wherein the cloud server is configured to execute programs or scripts to respond to a plurality of requests from the user device;

configuring a first acoustic wave communication module to encode an atomizing device activation signal into a first acoustic wave signal to be transmitted when the communication module receives the authentication success signal;

configuring a second acoustic communication module of the atomization device to receive the first acoustic signal, and decode the first acoustic signal to produce a starting signal for the atomization device; and configuring a control module of the atomization device to control the atomization module to atomize the atomized medicine according to the starting signal for the atomization device;

wherein the atomization method further includes configuring the optical authentication module to perform a second optical authentication operation related to the authentication code carrier to obtain second optical authentication information;

wherein the second optical authentication operation includes at least one of a gesture authentication, a face recognition authentication, and a fingerprint identification authentication.

11. The atomization method having the authentication mechanism according to claim 10, wherein after the control module controls the atomization module to atomize the atomized medicine, the method further includes:

configuring the control module to generate a starting state signal;

configuring the second acoustic wave communication module to encode the starting state signal into a second acoustic wave signal to be transmitted; and configuring the first acoustic communication module to receive and decode the second acoustic signal to display a starting state of the atomization device on the user device.

12. The atomization method having an authentication mechanism according to claim 10, wherein each of the first acoustic communication module and the second acoustic communication module includes:

an acoustic wave signal generator, configured to transmit acoustic wave signals;

an acoustic wave receiver, configured to receive acoustic wave signals; and an acoustic wave signal processing module, configured to decode the received acoustic wave signals to generate a signal, and encode the signal to generate an acoustic wave signal.

13. The atomization method having the authentication mechanism according to claim 12, wherein the acoustic wave signals include at least one of an audible sound wave, an inaudible sound wave, a dual tone multi-frequency sound wave, and an ultrasonic wave.

14. The atomization method having the authentication mechanism according to claim 10, wherein the first optical authentication operation includes: identifying, by the optical authentication module, an authentication code of the authentication code carrier to obtain the first optical authentication information.

15. The atomization method having the authentication mechanism according to claim 14, wherein the authentication code includes at least one of a barcode, a QR code, and a dot matrix pattern.

16. The atomization method having the authentication mechanism according to claim 10, further including:

configuring an authentication module of the user device to perform an authentication operation for the second optical authentication information, and the user device performs the first authentication operation after the authentication operation is completed.

17. The atomization method having the authentication mechanism according to claim 10, further comprising:

using an authentication information input interface to input authentication information on the authentication code carrier; and configuring the communication module to request the cloud server to perform the authentication operation for the authentication information to determine the authenticity of the atomized medicine container, wherein after the authentication operation is completed, the cloud server returns the authentication success signal.

18. The atomization method having the authentication mechanism according to claim 10, further including:

using an authentication information input interface of the user device to input authentication information on the authentication code carrier; and configuring an authentication module to perform an authentication operation for the authentication information to determine the authenticity of the atomized medicine container, wherein after the authentication operation is completed, the first acoustic wave communication module is configured to directly encode the starting signal for the atomization device as the first acoustic signal to be transmitted.

* * * * *